US009903711B2

(12) United States Patent
Levy et al.

(10) Patent No.: US 9,903,711 B2
(45) Date of Patent: Feb. 27, 2018

(54) FEED FORWARD OF METROLOGY DATA IN A METROLOGY SYSTEM

(71) Applicant: KLA-Tencor Corporation, Milpitas, CA (US)

(72) Inventors: Ady Levy, San Jose, CA (US); Daniel Kandel, Aseret (IL); Michael E. Adel, Ya'akov (IL); Leonid Poslavsky, Belmont, CA (US); John Robinson, Austin, TX (US); Tal Marciano, Yokneam (IL); Barak Bringoltz, Le Tzion (IL); Tzahi Grunzweig, Yokneam (IL); Dana Klein, Haifa (IL); Tal Itzkovich, kfar Uriya (IL); Nadav Carmel, Mevasseret-Zion (IL); Nuriel Amir, Yokne'am Ilit (IL); Vidya Ramanathan, Milpitas, CA (US); Janay Camp, Milpitas, CA (US); Mark Wagner, Rehovot (IL)

(73) Assignee: KLA—Tencor Corporation, Milpitas, CA (US)

( * ) Notice: Subject to any disclaimer, the term of this patent is extended or adjusted under 35 U.S.C. 154(b) by 0 days.

(21) Appl. No.: 15/090,389

(22) Filed: Apr. 4, 2016

(65) Prior Publication Data
US 2016/0290796 A1    Oct. 6, 2016

Related U.S. Application Data

(60) Provisional application No. 62/143,689, filed on Apr. 6, 2015, provisional application No. 62/161,982, filed on May 15, 2015.

(51) Int. Cl.
*G01B 11/14* (2006.01)
*G01B 11/27* (2006.01)
(Continued)

(52) U.S. Cl.
CPC ....... *G01B 11/272* (2013.01); *G01N 21/9501* (2013.01); *G03F 7/705* (2013.01);
(Continued)

(58) Field of Classification Search
CPC ... G01B 11/272; G01B 11/00; G01B 11/0641; G01N 21/9501; G01N 21/21;
(Continued)

(56) References Cited

U.S. PATENT DOCUMENTS 5,608,526 A    3/1997 Piwonka-Corle et al.
5,859,424 A    1/1999 Norton et al.
(Continued)

OTHER PUBLICATIONS

PCT Search Report for PCT/US2016/026060, dated Jun. 30, 2016, 3 pages.

*Primary Examiner* — Jamil Ahmed
(74) *Attorney, Agent, or Firm* — Suiter Swantz pc llo

(57) ABSTRACT

A metrology performance analysis system includes a metrology tool including one or more detectors and a controller communicatively coupled to the one or more detectors. The controller is configured to receive one or more metrology data sets associated with a metrology target from the metrology tool in which the one or more metrology data sets include one or more measured metrology metrics and the one or more measured metrology metrics indicate deviations from nominal values. The controller is further configured to determine relationships between the deviations from the nominal values and one or more selected semiconductor process variations, and determine one or more root causes of the deviations from the nominal values based on the relationships between values of the one or more metrology metrics and the one or more selected semiconductor process variations.

33 Claims, 9 Drawing Sheets

(51) Int. Cl.
*G01N 21/95* (2006.01)
*G03F 7/20* (2006.01)
*G01N 21/21* (2006.01)
*G01N 21/31* (2006.01)
*G01N 21/41* (2006.01)
*G01N 21/47* (2006.01)
*G01N 21/64* (2006.01)

(52) U.S. Cl.
CPC ...... *G03F 7/70525* (2013.01); *G03F 7/70533* (2013.01); *G03F 7/70616* (2013.01); *G01N 21/211* (2013.01); *G01N 21/31* (2013.01); *G01N 21/41* (2013.01); *G01N 21/4738* (2013.01); *G01N 21/4788* (2013.01); *G01N 21/6489* (2013.01); *G01N 2021/213* (2013.01)

(58) Field of Classification Search
CPC ...... G01N 21/211; G01N 21/31; G01N 21/41; G01N 21/4738; G01N 21/4788; G01N 21/6489; G01N 2021/213; G03F 7/705; G03F 7/70525; G03F 7/70616; G03F 1/36; G03F 7/70633; G06F 19/00; G06F 17/50; G05B 19/41875
See application file for complete search history.

(56) References Cited

U.S. PATENT DOCUMENTS

| | | |
|---|---|---|
| 6,429,943 B1 | 8/2002 | Opsal et al. |
| 6,985,618 B2 | 1/2006 | Adel et al. |
| 7,478,019 B2 | 1/2009 | Zangooie et al. |
| 7,933,026 B2 | 4/2011 | Opsal et al. |
| 2005/0192698 A1* | 9/2005 | Cheng ............ G05B 19/41875 700/121 |
| 2009/0037134 A1* | 2/2009 | Kulkarni ............ G01N 21/9501 702/127 |
| 2009/0259605 A1* | 10/2009 | Opsal ................ G01B 11/0641 706/15 |
| 2011/0080585 A1* | 4/2011 | Rabello ................ G01N 21/211 356/368 |
| 2012/0206729 A1 | 8/2012 | Seligson et al. |
| 2013/0003050 A1 | 1/2013 | Zhu et al. |
| 2013/0035888 A1* | 2/2013 | Kandel ............... G03F 7/70633 702/81 |
| 2013/0042089 A1 | 2/2013 | Vinh et al. |
| 2013/0304424 A1 | 11/2013 | Bakeman et al. |
| 2014/0089870 A1* | 3/2014 | Mos ......................... G03F 1/36 716/54 |
| 2014/0199791 A1 | 7/2014 | Park et al. |

* cited by examiner

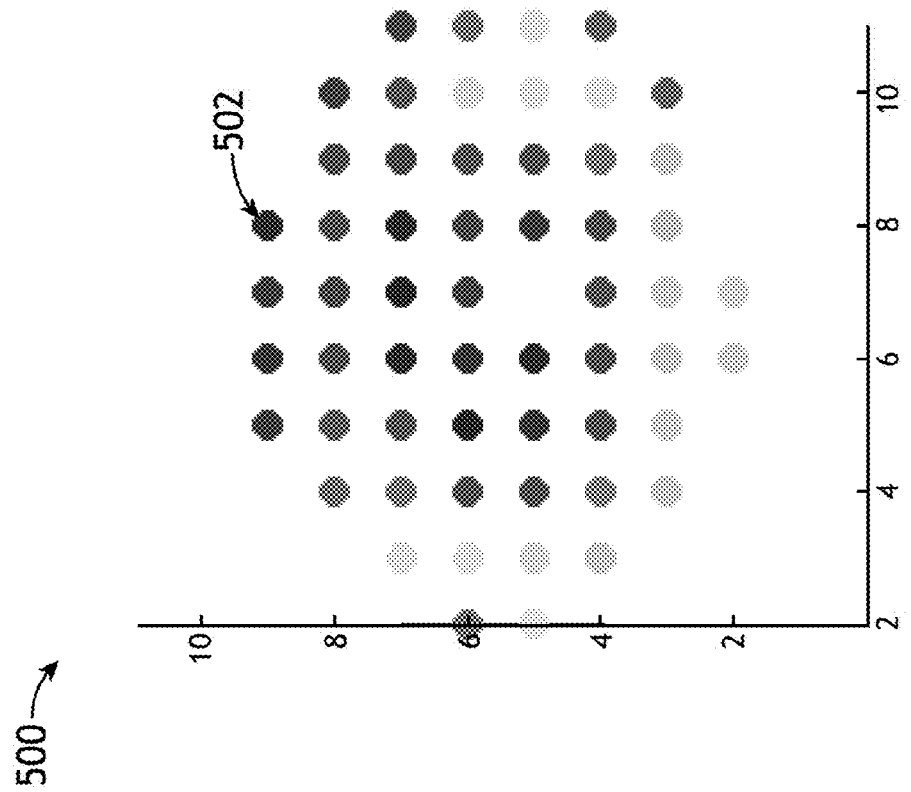

FEED FORWARD OF METROLOGY DATA IN A METROLOGY SYSTEM

CROSS-REFERENCE TO RELATED APPLICATION

The present application claims the benefit under 35 U.S.C. §119(e) of U.S. Provisional Application Ser. No. 62/143,689, filed Apr. 6, 2015, entitled FEED FORWARD OF METROLOGY DATA FOR METROLOGY TOOL SETUP OPTIMIZATION, which is incorporated herein by reference in the entirety.

The present application claims the benefit under 35 U.S.C. §119(e) of U.S. Provisional Application Ser. No. 62/161,982, filed May 15, 2015, entitled DETERMINING ROOT CAUSE OF PROCESS VARIATIONS WITH METROLOGY, which is incorporated herein by reference in the entirety.

TECHNICAL FIELD

The present disclosure relates generally to the field of metrology systems, and more particularly, to feed-forward of metrology data in metrology systems.

BACKGROUND

Semiconductor shape and placement metrology is challenged by constantly changing conditions in the characteristics of the wafer to be measured. Although it is the objective of all advanced process control methodologies to keep all manufacturing conditions stable with minimal temporal and spatial variation, this objective is in practice unattainable. Semiconductor processes performed by semiconductor process tools (e.g. lithographic tools, deposition tools, etch tools, polish tools, and the like) may drift over time, resulting in corresponding variations of the target wafer characteristics such as, but not limited to, composition, film thickness, feature size, or optical characteristics across the wafer or lot of wafers. These variations of target wafer characteristics may have a detrimental impact on subsequent metrology steps. For example, a film thickness variation of a particular layer across the wafer may result in varying accuracy or precision performance when an overlay metrology measurement is performed. Although targets may be designed for their robustness in the face of such variations, the range of tolerable variations to maintain tolerable metrology performance is bounded. If the variations extend beyond these bounds, a metrology performance excursion results, with a potential negative impact on the process control.

SUMMARY

A metrology performance analysis system is disclosed in accordance with one or more illustrative embodiments of the present disclosure. In one illustrative embodiment, the system includes a metrology tool including one or more detectors. In another illustrative embodiment, the system includes a controller communicatively coupled to the one or more detectors. In another illustrative embodiment, the controller includes one or more processors configured to execute program instructions. In another illustrative embodiment, the one or more processors are configured to execute program instructions configured to cause the one or more processors to receive one or more metrology data sets associated with a metrology target from the metrology tool. In another illustrative embodiment, the one or more metrology data sets include one or more measured metrology metrics. In another illustrative embodiment, the one or more measured metrology metrics indicate one or more deviations from one or more nominal values. In another illustrative embodiment, the one or more processors are configured to execute program instructions configured to cause the one or more processors to determine one or more relationships between the one or more deviations from the one or more nominal values and one or more selected semiconductor process variations. In another illustrative embodiment, the one or more processors are configured to execute program instructions configured to cause the one or more processors to determine one or more root causes of the one or more deviations from the one or more nominal values based on the one or more relationships between the one or more deviations from the one or more nominal values and the one or more selected semiconductor process variations.

A metrology performance analysis system is disclosed, in accordance with one or more illustrative embodiments of the present disclosure. In one illustrative embodiment, the system includes a metrology tool including one or more detectors. In another illustrative embodiment, the system includes a controller communicatively coupled to the one or more detectors. In another illustrative embodiment, the controller includes one or more processors configured to execute program instructions. In another illustrative embodiment, the one or more processors are configured to execute program instructions configured to cause the one or more processors to receive one or more metrology data sets associated with a metrology target from the metrology tool. In another illustrative embodiment, the one or more metrology data sets include one or more measured metrology metrics. In another illustrative embodiment, the one or more measured metrology metrics indicate one or more deviations from one or more nominal values. In another illustrative embodiment, the one or more metrology data sets are generated using a first recipe. In another illustrative embodiment, the one or more processors are configured to execute program instructions configured to cause the one or more processors to determine one or more relationships between the one or more deviations from the one or more nominal values and one or more selected semiconductor process variations. In another illustrative embodiment, the one or more processors are configured to execute program instructions configured to cause the one or more processors to determine one or more root causes of the one or more deviations from the one or more nominal values based on the one or more relationships between the one or more deviations from the one or more nominal values and the one or more selected semiconductor process variations. In another illustrative embodiment, the one or more processors are configured to execute program instructions configured to cause the one or more processors to direct the metrology tool to generate one or more additional measured metrology metrics associated with at least one additional metrology target using a second recipe, wherein the second recipe reduces a sensitivity of the metrology tool to the one or more root causes.

A method for analyzing the performance of a metrology system is disclosed, in accordance with one or more illustrative embodiments of the present disclosure. In one illustrative embodiment, the method includes receiving one or more metrology data sets associated with a metrology target. In another illustrative embodiment, the one or more metrology data sets include one or more measured metrology metrics. In another illustrative embodiment, the one or more measured metrology metrics indicate deviations from nominal values. In another illustrative embodiment, the method includes determining one or more relationships between the one or more deviations from the one or more nominal values and one or more selected semiconductor process variations. In another illustrative embodiment, the method includes determining one or more root causes of the one or more deviations from the one or more nominal values based on the one or more relationships between the one or more deviations from the one or more nominal values and the one or more selected semiconductor process variations.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which:

FIG. 5 includes a sample map illustrating a variation of the position of an arc of discontinuity in the pupil plane as a function of location on the sample, in accordance with one or more embodiments of the present disclosure.

DETAILED DESCRIPTION

Figure 1A:
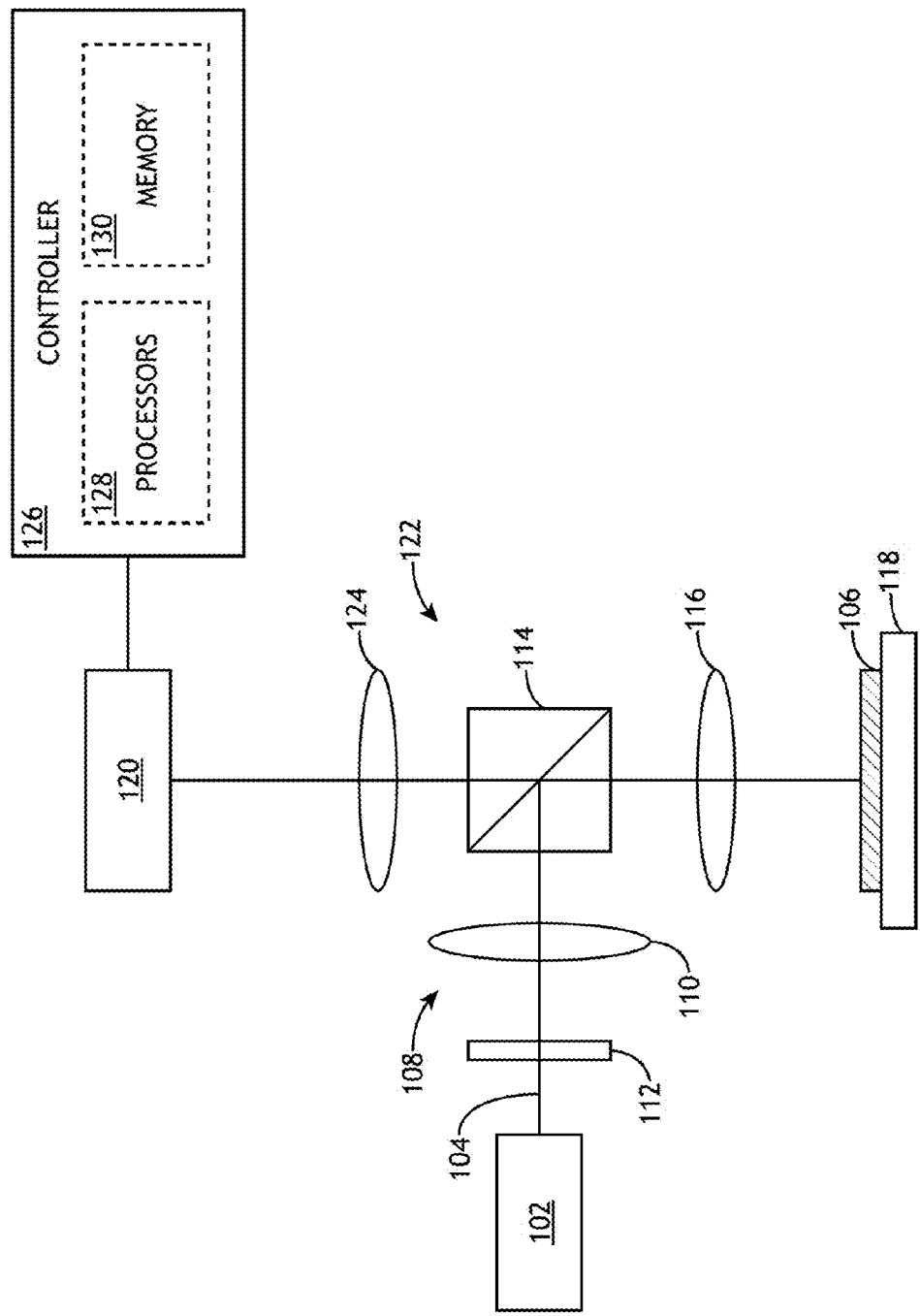
FIG. 1A is a block diagram view of a metrology system, in accordance with one or more embodiments of the present disclosure.

Reference will now be made in detail to the subject matter disclosed, which is illustrated in the accompanying drawings.

Referring generally to FIGS. 1A through 8, a system and method for feed-forward metrology data for determining a root cause of process variations is described, in accordance with one or more embodiments of the present disclosure. Embodiments of the present disclosure are directed to simulating metrology measurements of a modeled metrology target. Additional embodiments of the present disclosure are directed to perturbing the metrology target according to one or more process variations and simulating metrology measurements of the perturbed metrology target. Additional embodiments of the present disclosure are directed to performing metrology measurements on a real metrology target and determining one or more root causes of metrology errors by identifying one or more semiconductor process variations responsible for the metrology errors. Further embodiments of the present disclosure are directed to predicting and/or mediating drifts of one or more process variations prior to a metrology excursion.

It is recognized herein that semiconductor processes (e.g. deposition of a film, a lithography step, an etch step, and the like) performed by a semiconductor process tool may drift over time. Drift may be a result of a multitude of factors including, but not limited to, tool wear or drift in a control algorithm associated with the process. Further, the drift may affect one or more characteristics of a sample, which may, in turn, affect one or more metrology measurements (e.g. overlay measurements, surface profile measurements, and the like). For example, a film thickness variation of a particular layer across the wafer may result in varying accuracy or precision performance when an overlay metrology measurement is performed. Although metrology targets may be designed to provide robust performance in the presence of semiconductor process variations, deviations of a target feature (e.g. surface profile, film thickness, and the like) beyond a threshold value may result in performance outside of a specified tolerance, indicating a performance excursion. Further, the robustness of a metrology target to a particular process variation may be dependent on the specific configuration, or recipe, of the metrology tool (e.g. a wavelength of light or a polarization of light utilized to perform a metrology measurement, and the like) as well as the optical characteristics of the metrology target (e.g. a thickness of one or more films, diffraction effects, and the like).

It is further recognized herein that an excursion associated with a deviation of a metrology measurement outside of a tolerance range may have a negative impact on process control within a semiconductor fabrication line. Further, the detection of an excursion may necessitate a temporary halt to manufacturing to determine a root cause of the excursion (e.g. determining one or more drifting semiconductor processes, troubleshooting of the metrology tool, rework of the metrology tool setup, and the like).

Embodiments of the present disclosure are directed to utilizing metrology data to determine a deviation of metrology performance (e.g. overlay performance, and the like). It is noted that metrology tools may provide various outputs including, but not limited to, metrology data (e.g. metrology measurement results, images of the target, pupil images, and the like) or metrology metrics (e.g. precision, tool-induced shift, sensitivity, diffraction efficiency, through-focus slope, side wall angle, critical dimensions, and the like). Additional embodiments are directed to determining a root cause associated with the deviation of metrology performance such as, but not limited to, a variation of a semiconductor process (e.g. associated with a drift of the semiconductor process tool). Further embodiments are directed to providing feed-forward data to the metrology tool and/or additional metrology tools. In this regard, feed-forward data including data associated with a variation of a semiconductor process and/or a variation in metrology measurements associated with the variation of the semiconductor process may be utilized by the same tool (e.g. on a different die, on a different lot of the same process, or the like) or by one or more additional tools in the semiconductor fabrication line to mitigate the root causes and prevent or minimize metrology excursions.

As used throughout the present disclosure, the term "sample" generally refers to a substrate formed of a semiconductor or non-semiconductor material including one or more "layers" or "films", and patterned structures which are usually chosen to be periodic for optical metrology. For example, semiconductor or non-semiconductor materials include, but are not limited to, monocrystalline silicon, gallium arsenide, and indium phosphide. Layers formed on the substrate may include, but are not limited to, a resist, a dielectric material, a conductive material, or a semiconductive material. Many different types of sample layers are known in the art, and the term sample as used herein is intended to encompass a substrate and any types of layers formed thereon.

Embodiments of the present disclosure may incorporate any type of metrology system known in the art including, but not limited to, a spectroscopic ellipsometer with one or more angles of illumination, a spectroscopic ellipsometer for measuring Mueller matrix elements (e.g. using rotating compensators), a single-wavelength ellipsometer, an angle-resolved ellipsometer (e.g. a beam-profile ellipsometer), a spectroscopic reflectometer, a single-wavelength reflectometer, an angle-resolved reflectometer (e.g. a beam-profile reflectometer), an imaging system, a pupil imaging system, a spectral imaging system, or a scatterometer. Further, the metrology system may include a single metrology tool or multiple metrology tools. A metrology system incorporating multiple metrology tools is generally described in U.S. Pat. No. 7,478,019. Focused beam ellipsometry based on primarily reflective optics is generally described in U.S. Pat. No. 5,608,526, which is incorporated herein by reference in its entirety. The use of apodizers to mitigate the effects of optical diffraction causing the spread of the illumination spot beyond the size defined by geometric optics is generally described in U.S. Pat. No. 5,859,424, which is incorporated herein by reference in its entirety. The use of high-numerical-aperture tools with simultaneous multiple angle-of-incidence illumination is generally described by U.S. Pat. No. 6,429,943, which is incorporated herein by reference in its entirety.

It is further recognized herein that a metrology tool may measure characteristics of one or more targets such as, but not limited to, critical dimensions (CD), overlay, sidewall angles, film thicknesses, or process-related parameters (e.g. focus, dose, and the like). The targets may include certain regions of interest that are periodic in nature, such as gratings in a memory die. The metrology targets may further possess various spatial characteristics and are typically constructed of one or more cells which may include features in one or more layers which may have been printed in one or more lithographically distinct exposures. The targets or the cells may possess various symmetries such as two-fold or four-fold rotation symmetry, reflection symmetry. Examples of such metrology structures are described in U.S. Pat. No. 6,985,618, which is included herein by reference in its entirety. Different cells or combinations of cells may belong to distinct layers or exposure steps. The individual cells may comprise either isolated non-periodic features or alternately they may be constructed from one, two, or three dimensional periodic structures or combinations of non-periodic and periodic structures. The periodic structures may be non-segmented or they may be constructed from finely segmented features which may at or close to the minimum design rule of the lithographic process used to print them. The metrology targets may also be collocated or in close proximity with dummification structures in the same layer or in a layer above, below, or in between the layers of the metrology structures. Targets can include multiple layers (e.g., films) whose thicknesses can be measured by the metrology tool. Targets can include target designs placed on the semiconductor wafer for use (e.g., with alignment, overlay registration operations, and the like). Further, targets may be located at multiple sites on the semiconductor wafer. For example, targets may be located within scribe lines (e.g., between dies) and/or located in the die itself. Multiple targets may be measured simultaneously or serially by the same or multiple metrology tools as described in U.S. Pat. No. 7,478,019, which is incorporated herein by reference in its entirety. Metrology data from the metrology tool may be utilized in the semiconductor manufacturing process for example to feed-forward, feed-backward and/or feed-sideways corrections to the process (e.g., a lithography step, an etch step, or the like) to provide a complete process-control solution.

FIG. 1A is a block diagram view of a metrology system, in accordance with one or more embodiments of the present disclosure. In one embodiment, the system 100 includes a metrology sub-system including an illumination source 102 configured to generate an illumination beam 104. For example, the illumination beam 104 may include one or more selected wavelengths of light including, but not limited to, ultraviolet (UV) radiation, visible radiation, or infrared (IR) radiation. In another embodiment, the wavelengths of radiation of the illumination beam 104 emitted by the illumination source 102 are tunable. In this regard, the wavelengths of radiation of the illumination beam 104 may be adjusted to any selected wavelength of radiation (e.g. UV radiation, visible radiation, infrared radiation, or the like). Further, the illumination beam 104 may include one or more beams of radiation.

The illumination source 102 may include any illumination source known in the art suitable for generating an illumination beam 104. For example, the illumination source 102 may include, but is not limited to, a monochromatic light source (e.g. a laser), a polychromatic light source with a spectrum including two or more discrete wavelengths, a broadband light source, or a wavelength-sweeping light source. Further, the illumination source 102 may, but is not limited to, be formed from a white light source (e.g. a broadband light source with a spectrum including visible wavelengths), an laser source, a free-form illumination source, a single-pole illumination source, a multi-pole illumination source, an arc lamp, an electrode-less lamp, or a laser sustained plasma (LSP) source. Further, the illumination beam 104 may be delivered via free-space propagation or guided light (e.g. an optical fiber, a light pipe, or the like).

In another embodiment, the illumination source 102 directs the illumination beam 104 to a sample 106 via an illumination pathway 108. The illumination pathway 108 may include one or more lenses 110. Further, the illumination pathway 108 may include one or more additional optical components 112 suitable for modifying and/or conditioning the illumination beam 104. For example, the one or more optical components 112 may include, but are not limited to, one or more polarizers, one or more filters, one or more beam splitters, one or more diffusers, one or more homogenizers, one or more apodizers, or one or more beam shapers. In one embodiment, the illumination pathway 108 includes a beamsplitter 114. In another embodiment, the metrology sub-system includes an objective lens 116 to focus the illumination beam 104 onto one or more locations on the sample 106.

The illumination source 102 may direct the illumination beam 104 to the sample at any angle via the illumination pathway 108. In one embodiment, the illumination source 102 directs the illumination beam 104 to the sample 106 at normal incidence angle to a surface of the sample 106. In another embodiment, the illumination source 102 directs the illumination beam 104 to the sample 106 at an angle (e.g. a glancing angle, a 45-degree angle, and the like). In another embodiment, the angle of incidence of the illumination beam 104 on the sample 106 is adjustable. For example, the path of the illumination beam 104 through the beamsplitter 114 and the objective lens 116 may be adjusted to control the angle of incidence of the illumination beam 104 on the sample 106. In this regard, the illumination beam 104 may have a nominal path through the beamsplitter 114 and the objective lens 116 such that the illumination beam 104 has a normal incidence angle on the sample 106. Further, the angle of incidence of the illumination beam 104 on the sample 106 may be controlled by modifying the position and/or angle of the illumination beam 104 on the beamsplitter 114 (e.g. by rotatable mirrors, a spatial light modulator, a free-form illumination source, or the like).

In another embodiment, the system 100 includes a stage assembly 118 suitable for securing a sample 106. The stage assembly 118 may include any sample stage architecture known in the art. For example, the stage assembly 118 may include, but is not limited to, a linear stage. By way of another example, the stage assembly 118 may include, but is not limited to, a rotational stage. Further, the sample 106 may include a wafer, such as, but not limited to, a semiconductor wafer.

In another embodiment, the metrology sub-system includes one or more detectors 120 configured to capture radiation emanating from the sample 106 through a collection pathway 122. For example, a detector 120 may receive radiation reflected or scattered (e.g. via specular reflection, diffuse reflection, and the like) from the sample 106. As another example, a detector 120 may receive radiation generated by the sample (e.g. luminescence associated with absorption of the illumination beam 104, and the like). As an additional example, a detector 120 may receive one or more diffracted orders of radiation from the sample 106 (e.g. 0-order diffraction, ±1 order diffraction, ±2 order diffraction, and the like). Further, it is noted herein that the one or more detectors 120 may include any optical detector known in the art suitable for measuring illumination received from the sample 106. For example, a detector 120 may include, but is not limited to, a CCD detector, a TDI detector, a photomultiplier tube (PMT), an avalanche photodiode (APD), or the like. In another embodiment, a detector 120 may include a spectroscopic detector suitable for identifying wavelengths of radiation emanating from the sample 106. Further, the collection pathway 122 may include multiple optical elements to direct and/or modify illumination collected by the objective lens 116 including, but not limited to one or more lenses 124, one or more filters, one or more polarizers, one or more beam blocks, or one or more beamsplitters. Further, the metrology sub-system may include multiple detectors 120 (e.g. associated with multiple beam paths generated by one or more beamsplitters to facilitate multiple metrology measurements (e.g. multiple metrology tools) by the metrology sub-system.

In another embodiment, the system 100 includes a controller 126 communicatively coupled to the detector 120. For example, the controller 126 may be configured to receive metrology data including, but not limited to, metrology data (e.g. metrology measurement results, images of the target, pupil images, and the like) or metrology metrics (e.g. precision, tool-induced shift, sensitivity, diffraction efficiency, through-focus slope, side wall angle, critical dimensions, and the like). In another embodiment, the controller 126 is communicatively coupled to the illumination source 102. For example, the controller 126 may direct the illumination source 102 to provide one or more selected wavelengths of illumination (e.g. in response to feedback). In a general sense, the controller 126 may be communicatively coupled with any element within the metrology sub-system. In another embodiment, the controller 126 is communicatively coupled to the optical components 112 and/or the illumination source 102 to direct the adjustment of the angle of incidence between the illumination beam 104 and the sample 106. Further, the controller 126 may analyze data received from the detector 120 and feed the data to additional components within the metrology sub-system or external to the system 100. It is recognized herein that the steps described throughout the present disclosure may be carried out by a single controller 126 or, alternatively, multiple controllers 126. It is further noted herein that the one or more controllers 126 may be housed in a common housing or within multiple housings. In this way, any controller or combination of controllers may be separately packaged as a module suitable for integration into a complete system 100.

In another embodiment, the controller 126 includes one or more processors 128. In another embodiment, the one or more processors 128 are configured to execute a set of program instructions maintained in a memory medium 130, or memory. Further, the controller 126 may include one or more modules (e.g. a metrology performance analysis module, or the like) including one or more program instructions stored in the memory medium 130 and executed by the one or more processors 128. The one or more processors 128 of a controller 126 may include any processing element known in the art. In this sense, the one or more processors 128 may include any microprocessor-type device configured to execute algorithms and/or instructions. In one embodiment, the one or more processors 128 may consist of a desktop computer, mainframe computer system, workstation, image computer, parallel processor, or any other computer system (e.g., networked computer) configured to execute a program configured to operate the system 100, as described throughout the present disclosure. It is further recognized that the term "processor" may be broadly defined to encompass any device having one or more processing elements, which execute program instructions from a non-transitory memory medium 130.

The memory medium 130 may include any storage medium known in the art suitable for storing program instructions executable by the associated one or more processors 128. For example, the memory medium 130 may include a non-transitory memory medium. As an additional example, the memory medium 130 may include, but is not limited to, a read-only memory, a random access memory, a magnetic or optical memory device (e.g., disk), a magnetic tape, a solid state drive and the like. It is further noted that memory medium 130 may be housed in a common controller housing with the one or more processors 128. In one embodiment, the memory medium 130 may be located remotely with respect to the physical location of the one or more processors 128 and controller 126. For instance, the one or more processors 128 of controller 126 may access a remote memory (e.g., server), accessible through a network (e.g., internet, intranet and the like). Therefore, the above description should not be interpreted as a limitation on the present invention but merely an illustration.

Figure 1B:
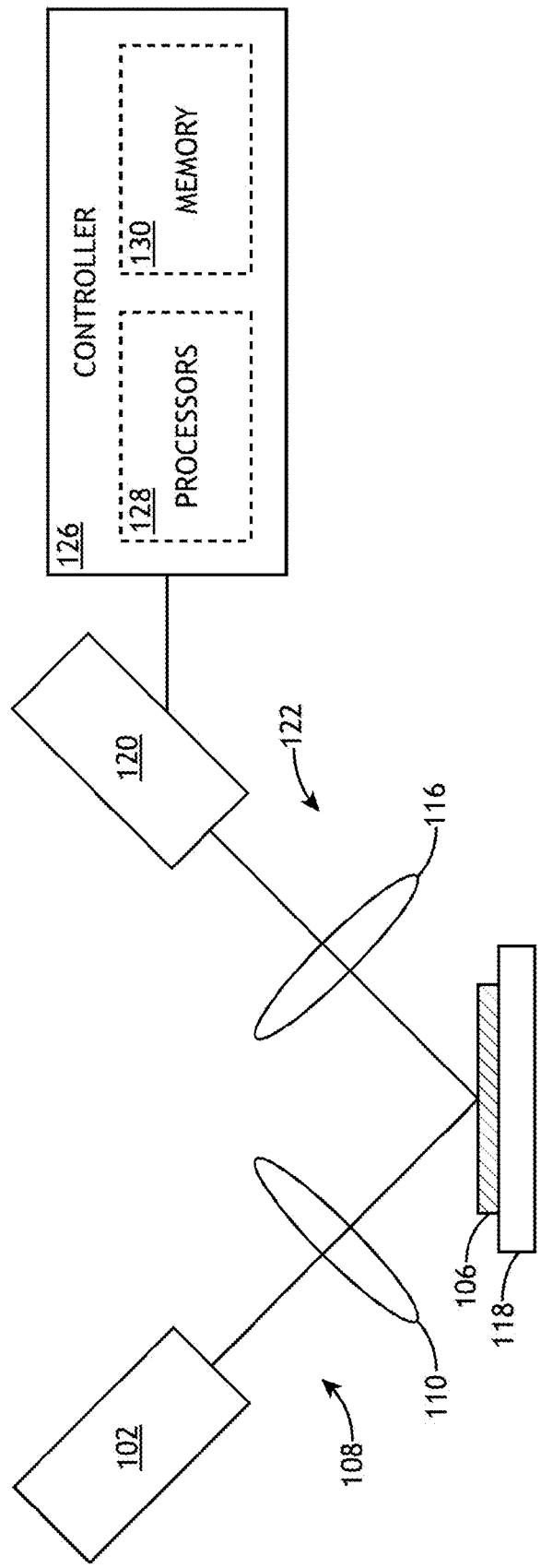
FIG. 1B is a block diagram view of a metrology system, in accordance with one or more embodiments of the present disclosure.

FIG. 1B is a block diagram view of a metrology system, in accordance with one or more embodiments of the present disclosure. The system 100 depicted in FIG. 1B may represent an alternative embodiment to the system 100 described in FIG. 1A. In one embodiment, the illumination pathway 108 and the collection pathway 122 contain separate elements. For example, the illumination pathway 108 may utilize a first focusing element 110 to focus the illumination beam 104 onto the sample 106 and the collection pathway 122 may utilize a second focusing element 116 to collect radiation from the sample 106. In this regard, the numerical apertures of the first focusing element 110 and the second focusing element 116 may be different. Further, it is noted herein that the system 100 depicted in FIG. 1B may facilitate multi-angle illumination of the sample 106, and/or more than one illumination source 102 (e.g. coupled to one or more additional detectors 120). In this regard, the system 100 depicted in FIG. 1B may perform multiple metrology measurements. In another embodiment, one or more optical components 112 may be mounted to a rotatable arm (not shown) pivoting around the sample 106 such that the angle of incidence of the illumination beam 104 on the sample 106 may be controlled by the position of the rotatable arm.

Figure 2:
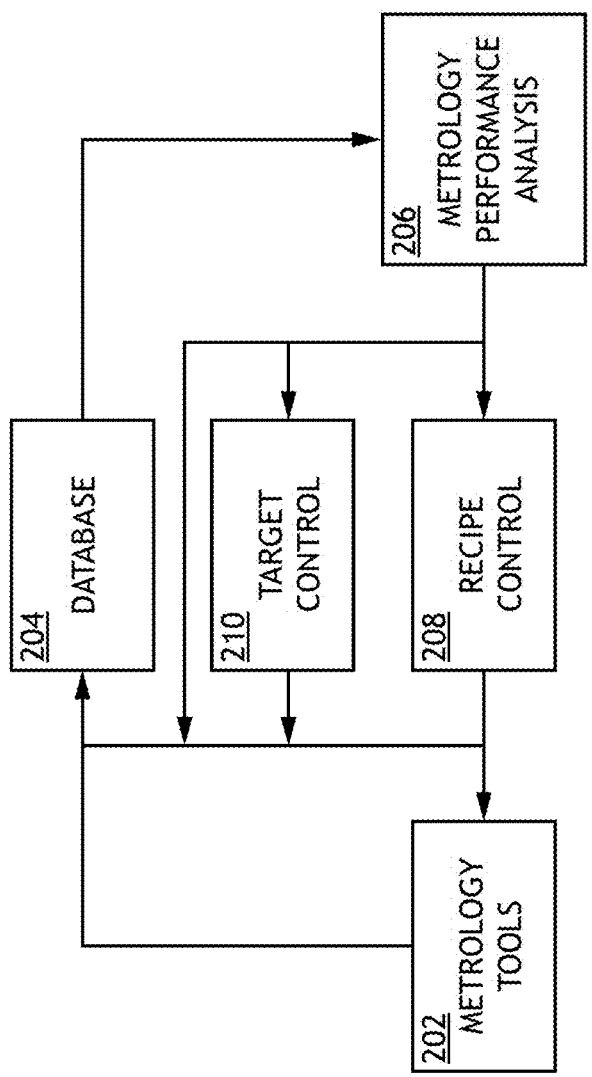
FIG. 2 is a block diagram illustrating a metrology system incorporating feedback, in accordance with one or more embodiments of the present disclosure.

FIG. 2 is a block diagram illustrating a system 100 incorporating feedback, in accordance with one or more embodiments of the present disclosure. In one embodiment, the system 100 includes one or more metrology tools 202. The metrology tools 202 associated with the system 100 may be associated with multiple stand-alone metrology tools 202 or combined within a single metrology system. In another embodiment, the metrology tools 202 provide as outputs metrology data (e.g. metrology measurement results, images of the target, pupil images, and the like) or metrology metrics (e.g. precision, tool-induced shift, sensitivity, diffraction efficiency, through-focus slope, side wall angle, critical dimensions, and the like). In another embodiment, the outputs of the metrology tools 202 are received by a database 204 to store the outputs of the metrology tools 202.

In another embodiment, the system 100 includes a metrology performance analysis module 206. In one embodiment, the metrology performance analysis module 206 receives metrology outputs (e.g. metrology data, metrology metrics, and the like) from the database 204 (e.g. metrology outputs associated with a current metrology target and/or one or more previously characterized metrology targets). In another embodiment, the metrology performance analysis module 206 receives metrology outputs directly from one or more of the metrology tools 202 (e.g. without using a database 204).

In another embodiment, the metrology performance analysis module 206 monitors the metrology outputs and identifies one or more deviations (e.g. of one or more metrology metrics, of one or more target characteristics, or the like) from nominal values. Further, the metrology performance analysis module 206 may identify one or more variations in one or more semiconductor processes associated with a metrology target that may contribute to the measured deviations of metrology outputs from the metrology tools 202. In one embodiment, the metrology performance analysis module 206 identifies symmetric process variations (e.g. a modification of a thickness of one or more films on the metrology target, or the like) and/or asymmetric process variations (e.g. an asymmetric etch profile, or the like) that may degrade the performance of the metrology target. For example, symmetric and/or asymmetric process variations may degrade the precision of an overlay measurement associated with an overlay target.

Further, the metrology performance analysis module 206 may identify a deviation in any type of semiconductor process associated with a metrology target including, but not limited to, film thickness parameters, real refractive index values as a function of wavelength, imaginary refractive index values as a function of wavelength (e.g. associated with one or more absorption peaks), local planarity, or stress/strain. Additionally, the metrology performance analysis module 206 may identify deviations in metrology target parameters such as, but not limited to, a critical dimension, induced topography, dishing, erosion, side wall angle, or asymmetry of side wall angle. In another embodiment, the metrology performance analysis module 206 identifies process variations or metrology target parameter variations between cells, between dies, as a function of location on the sample 106, across samples in a lot, across lots, and the like.

In another embodiment, the metrology analysis module 206 determines one or more root causes associated with identified deviations of the metrology outputs. For example, the metrology analysis module 206 may identify one or more process variations (e.g. drifts and/or process deviations associated with one or more semiconductor processes performed by a semiconductor process tool, or the like) that are responsible, at least in part, for measured deviations of metrology output. Further, the metrology analysis module 206 may characterize the one or more identified process variations as a function of location on the sample 106 (e.g. to generate a sample map of the identified process variations). The generation of a sample map of deviations of metrology data may be utilized by the controller 126 to facilitate identification of a root cause and/or to provide targeted feedback. For example, certain semiconductor processes may tend to display common process variations (e.g. chemical vapor deposition of an oxide film layer may tend to display a "sombrero profile" of the film thickness, chemical vapor deposition of a hard mask may tend to display a "domed" film thickness profile, or the like).

The identification of one or more root causes of deviations of one or more metrology outputs by the metrology performance analysis module 206 may be utilized by the system 100 to provide modifications (e.g. by feed-forward of metrology data) to additional metrology steps. In one embodiment, the metrology performance analysis module 206 provides metrology performance data (e.g. data associated with one or more identified process variations) to a recipe control module 208 for modification of a recipe of one or more additional metrology steps by the metrology tools 202. For example, a recipe of one or more of the metrology tools 202 may be modified to change the spatial sampling signature to compensate for deviations in a metrology metric (e.g. sensitivity or precision of an overlay metrology metric). As another example, a recipe of one or more of the metrology tools 202 may be modified (e.g. by adjusting a wavelength and/or a polarization of the illumination beam 104) to reduce the metrology performance dependence on the detected process variation. In another embodiment, metrology performance analysis module 206 provides metrology performance data (e.g. data associated with one or more identified process variations) to a target control module 210 to direct a modification of the metrology target (e.g. to one or more of the metrology tools 202 and/or a semiconductor process tool). For example, the target control module 210 may identify a metrology target that is less sensitive to the identified process variation. In another embodiment, data associated with the current metrology step is provided to the database 204 (e.g. the metrology performance analysis module 206 may provide metrology performance data, the recipe control module 208 may provide one or more recipes used by the metrology tools 202, the target control module 210 may provide one or more metrology targets characterized by the metrology tools 202, or the like). In another embodiment, metrology data associated with a simulation to measurement process is utilized to calibrate data for a root cause analysis.

It is noted herein that deviations of metrology performance may be compensated and/or mitigated through feedforward of metrology data. Further, the feed-forward of metrology data may maintain the performance of the system 100 within a specified tolerance and reduce or eliminate excursions. In one embodiment, metrology performance data provided by the metrology performance analysis module 206 may be sent to a system operator. For example, a system operator may be warned of a drift of one or more semiconductor processes (e.g. associated with one or more semiconductor process tools on a fabrication line) before an excursion. Accordingly a system operator may provide necessary maintenance to the corresponding semiconductor process tool and minimize any impact on the throughput of the fabrication line. In the case of a metrology excursion, the metrology performance data provided by the metrology performance analysis module 206 may provide additional information to enable corrective action at the source of the problem.

In another embodiment, metrology performance data associated with one or more previous metrology steps (e.g. provided by the database 204) is utilized to predict (e.g. through feed-forward metrology data) the impact of a variation of one or more semiconductor processes on a current metrology step. For example, the metrology performance analysis module 206 may calculate the anticipated metrology performance for multiple available metrology targets in order to identify an optimal metrology target for the current metrology step based on the feedback. As another example, the anticipated uncertainty or bias as a function of metrology sampling or overlay model may be calculated based on the feedback. Accordingly the metrology performance analysis module 206 may provide further feedback to the metrology tools 202 (e.g. through the recipe control module 208 and/or the target control module 210) to mitigate any anticipated performance deviations prior to the metrology measurement step based on the predicted impact of the identified process variation as a function of the recipe, metrology target, metrology sampling, or control model.

As an illustrative example, metrology data (e.g. film thickness, refractive index, and the like) may be generated by the metrology performance analysis module 206 as a function of location on the sample 106. In such a case, feedforward of metrology data to the metrology performance analysis module 206 (e.g. via the database 204) enables predications of the precision and accuracy of the fed forward metrology data as a function of location on the sample 106. Accordingly, the effect of the process variation on the value of the metrology model used to create exposure tool correctables may be predicted. Further, the bias and the residuals of the metrology model may be collected for any calculated variations of recipes and or metrology targets. In this regard the metrology parameters for the metrology tools 202 may be provided in advance of the current metrology step to optimize the exposure tool correctables or minimize model residuals. Additionally, the metrology performance analysis module 206 may provide feedback (e.g. as correctables, sampling variations, or the like) as part of an inspection system such as, but not limited to, an after-etch inspection system or an after-development inspection system. Further, the determination of a root cause of metrology data variations may provide a means to correlate data associated with an after-development inspection to after-etch inspection bias (e.g. to quantify effects associated with sacrificial layers on the sample 106).

In one embodiment, modification to a current metrology step based on feed-forward of metrology data is automatically generated (e.g. by the metrology performance analysis module 206) in real time for subsequent targets, dies, wafers, lots, or the like. In another embodiment, suggested modifications to a current metrology step based on feed-forward metrology data are provided to a system operator for verification and/or approval.

In another embodiment, metrology data (e.g. feed-forward metrology data) is utilized to optimize the sensitivity of the metrology tools 202 to one or more semiconductor processes (e.g. film thickness, etch asymmetry, and the like). For example, optimization of the sensitivity of the metrology tools 202 to semiconductor processes may provide an accurate determination of which of several semiconductor processes may be drifting. As another example, the metrology tools 202 may provide measurements of multiple recipes and/or metrology targets at one or more steps within the fabrication line to isolate the specific impacts of one or more process variations on metrology performance (e.g. to isolate and strengthen correlations between measured deviations of metrology data and one or more root causes of the deviations).

In another embodiment, the system 100 may utilize different recipes of the metrology tools 202 for different purposes. For example, a first recipe robust to process variations may be utilized for overlay measurements. Additionally, a second recipe sensitive to process variations may be utilized for root cause analysis. In this regard, the same metrology target may be used for multiple functions. In another embodiment, multiple metrology targets may be used (e.g. a first metrology target robust to process variations for overlay measurements and a second metrology target sensitive to process variations for root cause analysis). Further, the metrology targets and/or the recipes associated with the metrology tools 202 may be selected by the system through any method known in the art including, but not limited to, automatic recipe optimization. In another embodiment, metrics based on the combined measurement of two metrology targets and/or two recipes may be utilized to determine a root cause of measured metrology data variations. For example, a difference between a metrology measurement using a process-robust target and a metrology measurement using a process-sensitive target may provide a measure of the inaccuracy of the process-sensitive target to facilitate determination of the root cause.

In another embodiment, a metrology target (e.g. an overlay metrology target, or the like) may be analyzed after one or more processing steps to characterize the performance of the specific process steps metrology target to process variations (e.g. a variation of an optical path difference (OPD) that is a combination of the thickness and refractive index of a film layer, or the like). For example, the metrology performance analysis module 206 may, but is not limited to, monitor metrology data after one or more etching steps or after one or more lithography steps. Further, the metrology performance analysis module 206 may monitor a different set of metrology data after any of the process steps.

Figure 3:
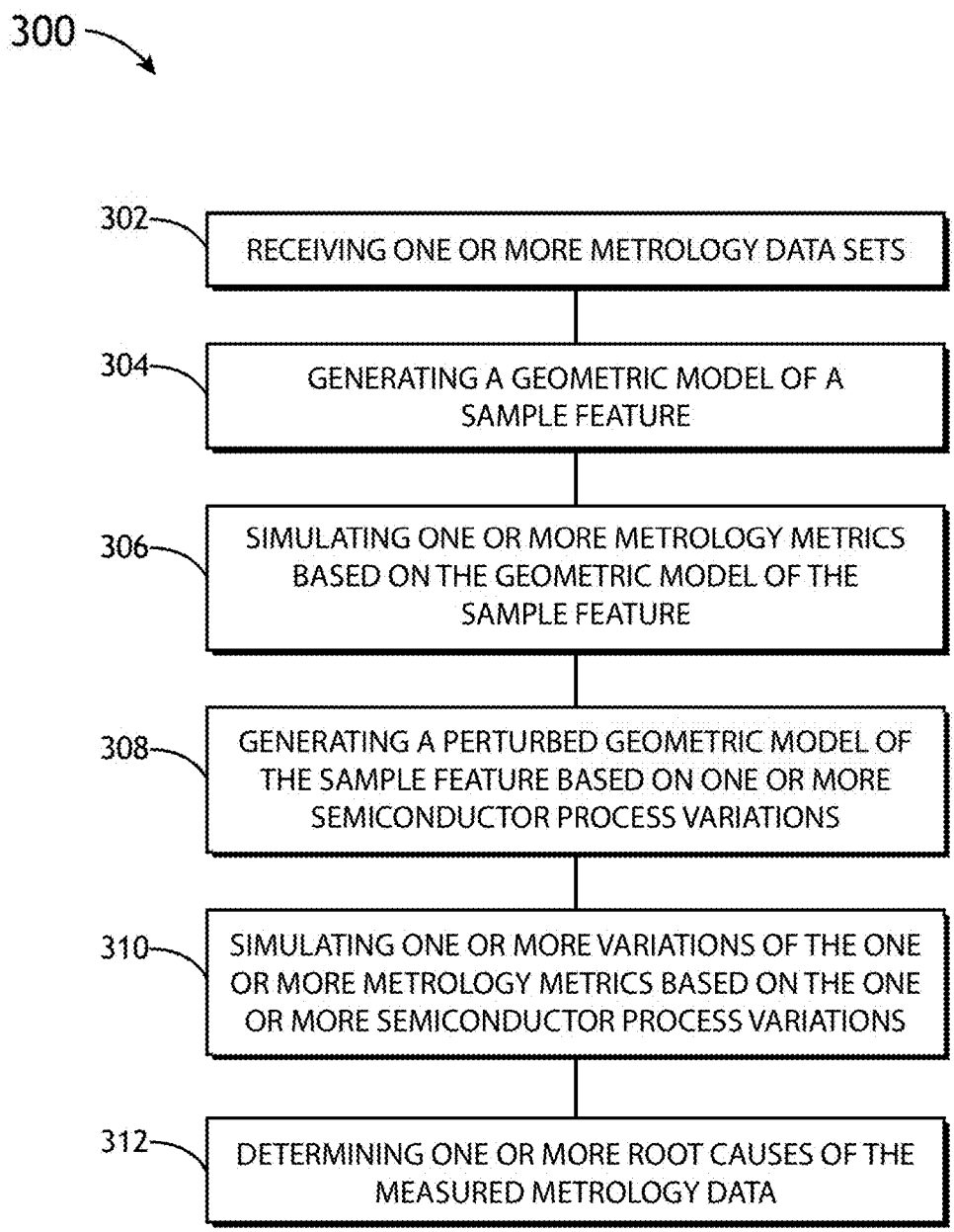
FIG. 3 is a flow diagram illustrating a method for analyzing the performance of a metrology system, in accordance with one or more embodiments of the present disclosure.

FIG. 3 is a flow diagram illustrating a method for analyzing the performance of a metrology system, in accordance with one or more embodiments of the present disclosure. Applicant notes that the embodiments and enabling technologies described previously herein in the context of system 100 should be interpreted to extend to method 300. It is further noted, however, that the method 300 is not limited to the architecture of system 100.

In one embodiment, the method 300 is associated with one or more command instructions stored on the memory medium 130 of the controller 126 and executed by the one or more processors 128. For example, method 300 may include an uncertainty analysis associated with the metrology target structure.

Step 302 illustrates receiving one or more metrology data sets. For example, a metrology performance analysis module 206 may receive one or more metrology data sets from the database 204 and/or the metrology tools 202, in accordance with one or more embodiments of the present disclosure. In one embodiment, the one or more metrology data sets include, but are not limited to, metrology data (e.g. metrology measurement results, images of the target, pupil images, and the like) or metrology metrics (e.g. precision, tool-induced shift, sensitivity, diffraction efficiency, through-focus slope, side wall angle, critical dimensions, and the like). In another embodiment, the metrology performance analysis module 206 identifies one or more values within the metrology data sets that represent deviations from nominal values. For example, pupil images associated with the metrology tools 202 may provide data (e.g. one or more features in a pupil image) indicative of one or more semiconductor process variations on the metrology target.

Step 304 illustrates generating a geometric model of a metrology target, in accordance with one or more embodiments of the present disclosure. For example, a geometric model of a metrology target (e.g. an overlay target, one or more features on the sample 106, or the like) may be generated by the metrology performance analysis module 206 or imported (e.g. by a system operator). In this regard a parameterized version of the metrology target is generated. Additionally, the use of a geometric engine for process modeling is implemented in the ACUSHAPE software product provided by KLA-TENCOR.

Step 306 illustrates simulating one or more metrology metrics based on the geometric model of the metrology target, in accordance with one or more embodiments of the present disclosure. In one embodiment, the metrology performance analysis module 206 predicts the values of one or more metrology metrics associated with one or more recipes and/or one or more metrology targets by the metrology tools 202. In one embodiment, the metrology tools 202 directly measure physical parameters associated with a metrology target (e.g. a surface profile, a spacing between one or more objects (e.g. of an overlay target), and the like). In another embodiment, one or more parameters of interest associated with a metrology data set are generated or verified using one or more computational models. For example, optical interaction of the illumination beam 104 with a metrology target on the sample 106 may, but is not limited to, be modeled using an electro-magnetic (EM) solver. Further, the EM solver may utilize any method known in the art including, but not limited to, rigorous coupled-wave analysis (RCWA), finite element method analysis, method of moments analysis, a surface integral technique, a volume integral technique, or a finite-difference time-domain analysis. Additionally, collected data may be analyzed using data fitting and optimization techniques including, but not limited to libraries, fast-reduced-order models, regression, machine-learning algorithms such as neural networks, support-vector machines (SVM), dimensionality-reduction algorithms (e.g. principal component analysis (PCA), independent component analysis (ICA), local-linear embedding (LLE), and the like), sparse representation of data (e.g. Fourier or wavelet transforms, Kalman filters, algorithms to promote matching from same or different tool types, and the like). For example, data collection and/or fitting may be, but is not required to be, performed by the Signal Response Metrology (SRM) software product provided by KLA-TENCOR.

In another embodiment, raw data generated by the metrology tools 202 is analyzed by algorithms that do not include modeling, optimization and/or fitting (e.g. phase characterization, or the like). It is noted herein that computational algorithms performed by the controller 126 may be, but are not required to be, tailored for metrology applications through the use of parallelization, distributed computation, load-balancing, multi-service support, design and implementation of computational hardware, or dynamic load optimization. Further, various implementations of algorithms may be, but are not required to be, performed by the controller 126 (e.g. through firmware, software, or field-programmable gate arrays (FPGAs), and the like), or one or more programmable optical elements associated with the metrology sub-system 100.

Step 308 illustrates generating a perturbed geometric model of the metrology target, in accordance with one or more embodiments of the present disclosure. In one embodiment, a geometric model of the metrology target (e.g. the model developed in step 304) is perturbed according to one or more selected semiconductor process variations. The perturbed geometric model may be generated by the metrology performance analysis module 206 or imported (e.g. by a system operator). For example, a thickness of one or more films associated with the geometric model of the metrology target may be modified. As another example, a real or imaginary refractive index value (e.g. associated with one or more wavelengths of radiation associated with a recipe of interest) of a component within the metrology target may be modified. As an additional example, a side-wall angle of one or more components of the metrology target (e.g. a grating-over-grating metrology overlay target) may be modified.

Step 310 illustrates simulating one or more variations of the one or more metrology metrics based on the one or more semiconductor process variations, in accordance with one or more embodiments of the present disclosure. In one embodiment, the metrology performance analysis module 206 repeats the computations and/or simulations performed in step 306 on the perturbed geometric model (e.g. the perturbed geometric model developed in step 308). In this regard, the metrology performance analysis module 206 may determine one or more relationships between one or more values of metrology metrics provided by the metrology tools 202 and the one or more selected semiconductor process variations modeled in step 308 (e.g. a variation of a thickness of one or more films associated with the metrology target, a real or imaginary refractive index value of a component within the metrology target, a side-wall angle of one or more components of the metrology target, or the like). In another embodiment, the resultant relationships between deviations of the metrology metrics and known semiconductor process variations are recorded (e.g. in the database 204).

Step 312 illustrates determining one or more root causes of the measured metrology data (e.g. including one or more deviations from nominal values) provided by the metrology tools 202. In one embodiment, the metrology performance analysis module 206 utilizes the one or more recorded relationships between one or more values of the one or more metrology metrics and the one or more selected semiconductor process variations generated in steps 304 through 310 to determine one or more semiconductor process variations that give rise to the metrology metrics measured in step 302. Further, the metrology performance analysis module 206 may generate a map of one or more semiconductor process as a function of location on the sample 106. For example, the metrology performance analysis module 206 may provide the thickness of a film across the surface of the sample 106 to determine that the thickness of the film is highest in the center and decreases towards the edges of the sample 106. The metrology performance analysis module 206 may further determine that the precision of a metrology target (e.g. an overlay target) may vary according to the radial position of the metrology target on the sample 106 due to a non-uniform application of the film. As another example, the metrology performance analysis module 206 may provide the side-wall angle of features on metrology targets to determine that the side-wall angle of the features, or asymmetry thereof, varies linearly across the surface of the sample 106. The metrology performance analysis module 206 may further determine that the precision of a metrology target (e.g. an overlay target) may vary according to the linear position of the metrology target on the sample 106 due to a deviation associated with an etching processing step.

It is noted herein that the description of the method 300 for analyzing the performance of a metrology system is provided solely for illustrative purposes and should not be interpreted as limiting. In another embodiment, the metrology performance analysis module 206 determines one or more root causes of one or more deviations of measured metrology metrics through a regression analysis. For example, the metrology performance analysis module 206 may utilize a regression analysis technique to determine relationships between geometric and optical parameters of a metrology target and metrology data such as real images and/or pupil images associated with the metrology tools 202. In another embodiment, the metrology performance analysis module 206 determines one or more root causes of one or more deviations of measured metrology metrics through a combination of simulation and regression analysis steps.

In another embodiment, the system 100 includes one or more metrology tools 202 operating as scatterometry overlay metrology tools. Further, a metrology performance analysis module 206 associated with a controller 126 within the system 100 may identify and evaluate semiconductor process variations through an analysis of pupil images of the metrology tools 202. The use of pupil images of metrology tools 202 as metrology metrics for the determination of one or more root causes of metrology data deviations (e.g. process variations that may impact overlay measurement performance) will now be described in more detail. For example, the metrology performance analysis module 206 may monitor one or more pupil features within pupil images of the metrology sub-system to identify both symmetric and asymmetric process variations. It is noted that the description of the use of pupil images of metrology tools 202 as metrology metrics for the determination of one or more root causes of metrology data deviations is provided solely for illustrative purposes and should not be interpreted as limiting. In a general sense, any metrology data generated by metrology tools 202 may be used for the determination of one or more root causes of metrology data deviations.

It is recognized herein that metrology targets (e.g. overlay targets, and the like) utilized in scatterometry overlay metrology tools typically include a grating-over-grating structure. For example, a cell of a grating-over-grating scatterometry overlay target may include a series of periodic structures (e.g. a diffraction grating) in one layer of the metrology target stacked above at least a second series of periodic structures in a second layer. In this regard, a cell of the metrology target is formed from at least two stacked diffraction gratings. Additionally, an overlay target may include multiple cells with different predetermined offsets (e.g. lateral translations) between the multiple diffraction gratings. In this regard, an overlay measurement measures an offset that is constant across each of the cells, which may in turn be associated with an alignment error of two layers of a semiconductor process.

It is further recognized herein that, in scatterometry overlay metrology tools, an illumination beam 104 incident on a metrology target on the sample 106 will generate a well-defined diffraction pattern that is detected at least in part by the detector 120. For example, a spectrometer located at an image plane may provide data associated with the wavelengths of radiation captured by the metrology tools 202 (e.g. wavelengths of radiation that enter through the entrance pupil). By way of another example, a detector 120 (e.g. a CCD detector) located at a pupil plane of a scatterometry overlay metrology tools may provide data associated with the angle at which light enters the system. In this regard, each pixel in the pupil plane measures the reflectivity of the metrology target associated with a different diffraction angle of the illumination beam 104.

Accordingly, an overlay measurement may be performed in a scatterometry overlay metrology tool by generating differential signals between measurements of each of the cells of the overlay target. For example, a scatterometry overlay metrology tool configured to measure zero-order diffraction from the metrology target may require measurements from four cells of the metrology target with different predetermined offsets to determine an overlay offset along a single direction. As another example, a scatterometry overlay metrology tool configured to measure first-order diffraction (e.g. +1 and −1 diffracted orders) from the metrology target may require measurements from two cells of the metrology target with different predetermined offsets to determine an overlay offset along a single direction. In this regard, a differential signal may be a pixel-by-pixel subtraction of measurements from each of the two cells of the metrology target.

In another embodiment, metrology metrics associated with the system 100 may be generated from differential signals. For example, the system 100 may generate multiple differential signals such as, but not limited to, $D_1 = S_{+1} - S_{-1}$, $D_2 = S_{+2} - S_{-2}$, $D_\alpha = S_{+1} - S_{-2}$, or $D_\beta = S_{+2} - S_{-1}$, where $S_{+1}$ and $S_{-1}$ are signals associated with the +/−1 diffraction orders from a first cell of the metrology target and $S_{+2}$ and $S_{-2}$ are signals associated with the +/−1 diffraction orders from a second cell of the metrology target. Further, the system 100 may generate additional quantities associated with the differential signals such as, but not limited to, $G=\alpha+\beta=(D_1-D_2)/2f_0$, or $\Delta=\alpha-\beta=(D_\alpha-D_\beta)/2f_0$, where $f_0$ is a predetermined offset (e.g. a lateral offset between a first and a second diffraction grating of a grating-over-grating metrology target). In this regard, the signal of the cells of the metrology target may be, but is not required to be, modeled as $S_{+1}=C+\alpha(\epsilon+f_0)$, $S_{-1}=C-\beta(\epsilon+f_0)$, $S_{+2}=C+\alpha(\epsilon-f_0)$, or $S_{-2}=C-\beta(\epsilon-f_0)$, where $\epsilon$ is indicative of the overlay error (e.g. a constant overlay between layers of the metrology target).

It is noted herein that any of the differential signals and/or quantities calculated from the differential signals may be utilized (e.g. by the metrology performance analysis module 206) to determine a correlation between metrology data and one or more process variations (e.g. in a root cause analysis). For example, the degree to which $\alpha$ differs from $\beta$, as well as the variability of this difference as a function of location across the surface of the sample 106 may facilitate determination of asymmetric process variations. As another example, the value of C may be calculated as an indicator of asymmetric process variations. As a further example, $\Delta$ may be provide data to facilitate determination of a model for the metrology to be used by the system 100 such as, but not limited to, a single-scattering model (e.g. associated with a metrology target including a single diffraction grating, or the like) or a multiple-scattering model (e.g. associated with a metrology target including multiple diffraction gratings, or the like). In this regard, in a single-scattering model, the signals $0_1 = f_0 \cdot D_\alpha/(D_1-D_2)$ and $0_2 = f_0 \cdot D_\beta/(D_1-D_2)$ may have equal contributions to a measured overlay value. Further, for the single-scattering model, the phase related to the optical path difference associated with the metrology target may be calculated as:

$$OPD = a\tan\left(\frac{(D_1+D_2)}{(D_\alpha-D_\beta)}\tan\left(\frac{2\pi f_0}{P}\right)\right)$$

where P is the pitch of the diffraction grating associated with the metrology target.

In one embodiment, the metrology performance analysis module 206 utilizes resonant effects associated with grating-over-grating metrology targets to identify, measure, and discriminate between different sources of process variations (e.g. symmetric and/or asymmetric process variations) as a function of location on the sample 106. In this regard, the pupil images of the scatterometry overlay metrology tools may form at least part of the metrology data associated with method 300. It is noted herein that a grating-over-grating metrology target may operate as a Fabry-Perot-like resonator such that the scatterometry overlay metrology tool may measure vanishing signal at specific wavelengths of radiation and/or angles of incidence on the entrance pupil. In this regard, the pupil plane of a metrology tool (e.g. a scatterometry overlay metrology tool, or the like) may include one or more features such as, but not limited to, an arc of discontinuity in the signal captured by detector 120 associated with vanishing sensitivity at a given pupil sensitivity location, or the like. Accordingly, the one or more pupil features may be metrology metrics utilized (e.g. by the metrology performance analysis module 206) to determine a root cause of deviations of metrology data.

Figures 4A, 4B:
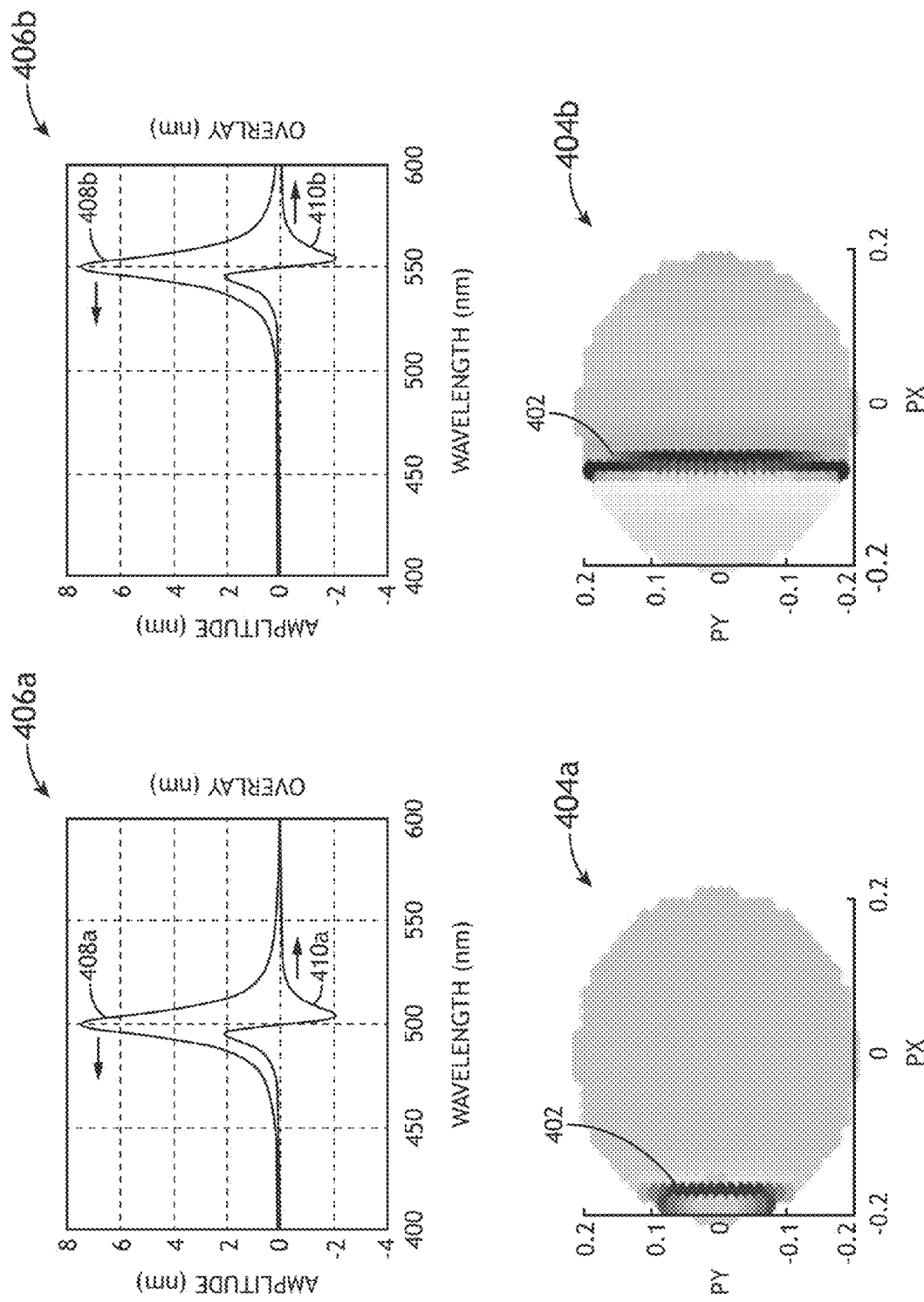
FIG. 4A includes metrology data of a scatterometry overlay metrology tool associated with a metrology targets illustrating a symmetric process variation at the metrology target, in accordance with one or more embodiments of the present disclosure.
FIG. 4B includes metrology data of a scatterometry overlay metrology tool associated with a metrology targets illustrating a symmetric process variation at the metrology target, in accordance with one or more embodiments of the present disclosure.

FIGS. 4A and 4B include metrology data of a scatterometry overlay metrology tool associated with two spatially separated metrology targets illustrating a symmetric process variation between the two targets, in accordance with one or more embodiments of the present disclosure. In one embodiment, the metrology performance analysis module 206 may detect a symmetric process variation (e.g. a variation of a film thickness, a variation of a critical dimension, or the like) between spatially separated metrology targets by monitoring variations in a location of an arc of discontinuity 402 within the pupil plane and/or a shift in a resonant wavelength associated with the grating-over-grating metrology target.

As illustrated in FIG. 4A, in one embodiment, a pupil image (e.g. a differential signal associated with cells of the metrology target) associated with a first metrology target at a first location on the sample 106 is shown as pupil signal 404a (e.g. with pupil coordinates PX and PY). Further, an arc of discontinuity 402 including a region of vanishing signal in the pupil plane (e.g. associated with light entering the system at a specified angle) is visible at a first location within the pupil plane. In another embodiment, a spectrum of radiation entering the pupil (e.g. as detected by a detector 120 at the image plane) is illustrated in spectrum 406a. A resonance signal 408a illustrates a resonance around a first wavelength (e.g. 500 nm as shown in FIG. 4). An error signal 410a illustrates a corresponding inaccuracy of an overlay measurement associated with the metrology target. The inaccuracy of the overlay measurement may, but is not limited to, represent a difference between an overlay as measured by the scatterometry overlay measurement tool using a process-sensitive recipe (e.g. including an arc of discontinuity 402) and the real overlay (e.g. as measured using a process-robust recipe or using a separate analysis). As illustrated in FIG. 4A, the error signal 410a may vary for wavelengths (e.g. wavelengths of the illumination beam 104) near the resonance wavelength.

As illustrated in FIG. 4B, in another embodiment, a pupil image (e.g. a differential signal associated with cells of the metrology target) associated with a second metrology target at a second location on the sample 106 is shown as pupil signal 404b (e.g. with pupil coordinates PX and PY). Further, the arc of discontinuity 402 is visible at a second location within the pupil plane. In another embodiment, a spectrum of radiation entering the pupil (e.g. as detected by a detector 120 at the image plane) is illustrated in spectrum 406b. The resonance and the corresponding error signal 410b associated with the resonance signal 408b are shifted relative to the resonance of the first metrology target (e.g. shifted to 550 nm as shown in FIG. 4B).

FIG. 5 includes a sample map 500 illustrating a variation of the position of the arc of discontinuity 402 in the pupil plane as a function of location on the sample 106, in accordance with one or more embodiments of the present disclosure. In this regard, each signal 502 provides a value associated with a monitored pupil feature (e.g. position of an arc of discontinuity 402, a resonance wavelength, or the like). In one embodiment, as shown in FIG. 5, a magnitude of the value associated with the monitored pupil feature indicating a symmetric process variation (e.g. a variation of a film thickness, a variation of a critical dimension, or the like) changes as a function of location on the sample 106 with a maximum near the center of the sample 106.

In another embodiment, the method 300 is applied to develop one or more correlations between known symmetric process variations and metrology data (e.g. a location of an arc of discontinuity 402 in a pupil plane, a resonance frequency, or the like). For example, certain film deposition processes such as, but not limited to chemical vapor deposition processes, produce thickness variations of a deposited film (e.g. a dome profile associated with deposition of a hard mask, a wavy profile associated with deposition of an oxide film, or the like). In one embodiment, the system 100 may identify a variation of a symmetric process on a sample 106 and provide metrology performance data (e.g. through the metrology performance analysis module 206 to the recipe control module 208) to modify a recipe for one or more metrology tools 202 to mitigate the impact of the symmetric performance variation on metrology performance. In another embodiment, the target control module 210 may identify different metrology targets (e.g. with different grating pitches) to be printed at different sites on the wafer to mitigate the impact of the symmetric performance variation on metrology performance.

Figure 6:
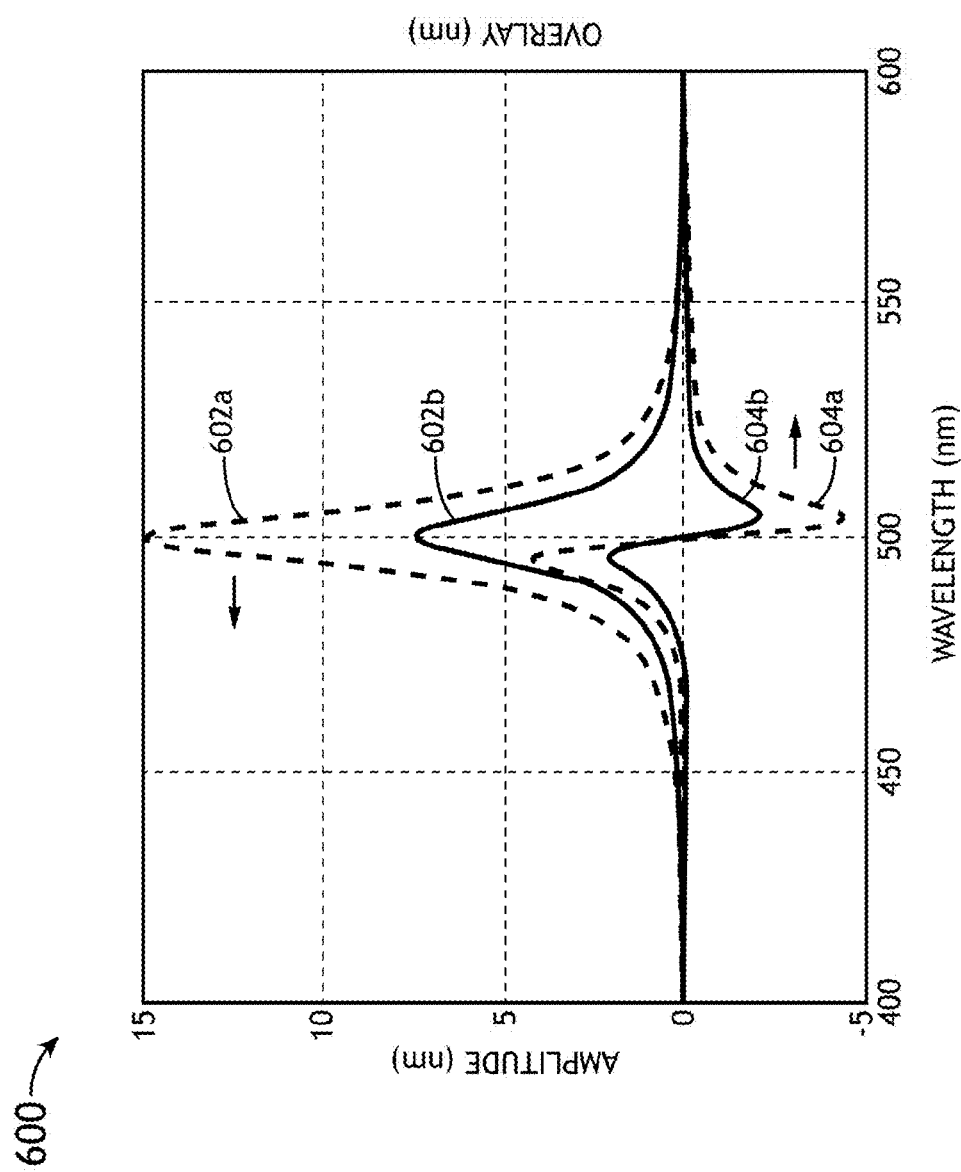
FIG. 6 includes metrology data of a scatterometry overlay metrology tool associated with two spatially separated metrology targets illustrating an asymmetric process variation of the same directionality between the two targets, in accordance with one or more embodiments of the present disclosure.

FIG. 6 includes metrology data 600 of a scatterometry overlay metrology tool associated with two spatially separated metrology targets illustrating an asymmetric process variation with the same directionality between the two targets, in accordance with one or more embodiments of the present disclosure. For example, two targets with an asymmetric process variation with the same directionality may include, but are not limited to, varying angles of a left-leaning side-wall. In one embodiment, the metrology performance analysis module 206 may detect an asymmetric process variation of the same directionality between spatially separated metrology targets by monitoring a strength of a resonance within the pupil plane and/or a trend of the measured overlay associated as a function of location on the sample 106. Additionally, the metrology performance analysis module 206 may detect an asymmetric process variation by monitoring the sign of the difference between the overlay measured in a resonant recipe (e.g. a recipe with a pupil feature such as, but not limited to, an arc of discontinuity) and the overlay measured in a robust recipe (e.g. a recipe without a pupil feature associated with resonance in the overlay target).

In another embodiment, resonance signals 602a, 602b illustrate a resonance associated with the spatially separated first and second metrology targets, respectively. Further, error signals 604a,604b illustrate corresponding inaccuracies of overlay measurements at the first and second metrology targets, respectively. For example, the sign of the inaccuracy (e.g. as characterized by a trend of overlay data as a function of location on the sample 106 or by comparison with a measurement using a robust recipe) may be the same for asymmetric process variations of the same directionality. However, the degree of asymmetric process variations of the same directionality may be characterized (e.g. by the metrology performance analysis module 206) by the strength of the resonance (e.g. as measured by a detector 120 located in an image plane of the metrology tools 202). Further, in one embodiment as shown in FIG. 6, an asymmetric process variation of the same directionality may not impact the resonance frequency in the pupil plane.

Figure 7:
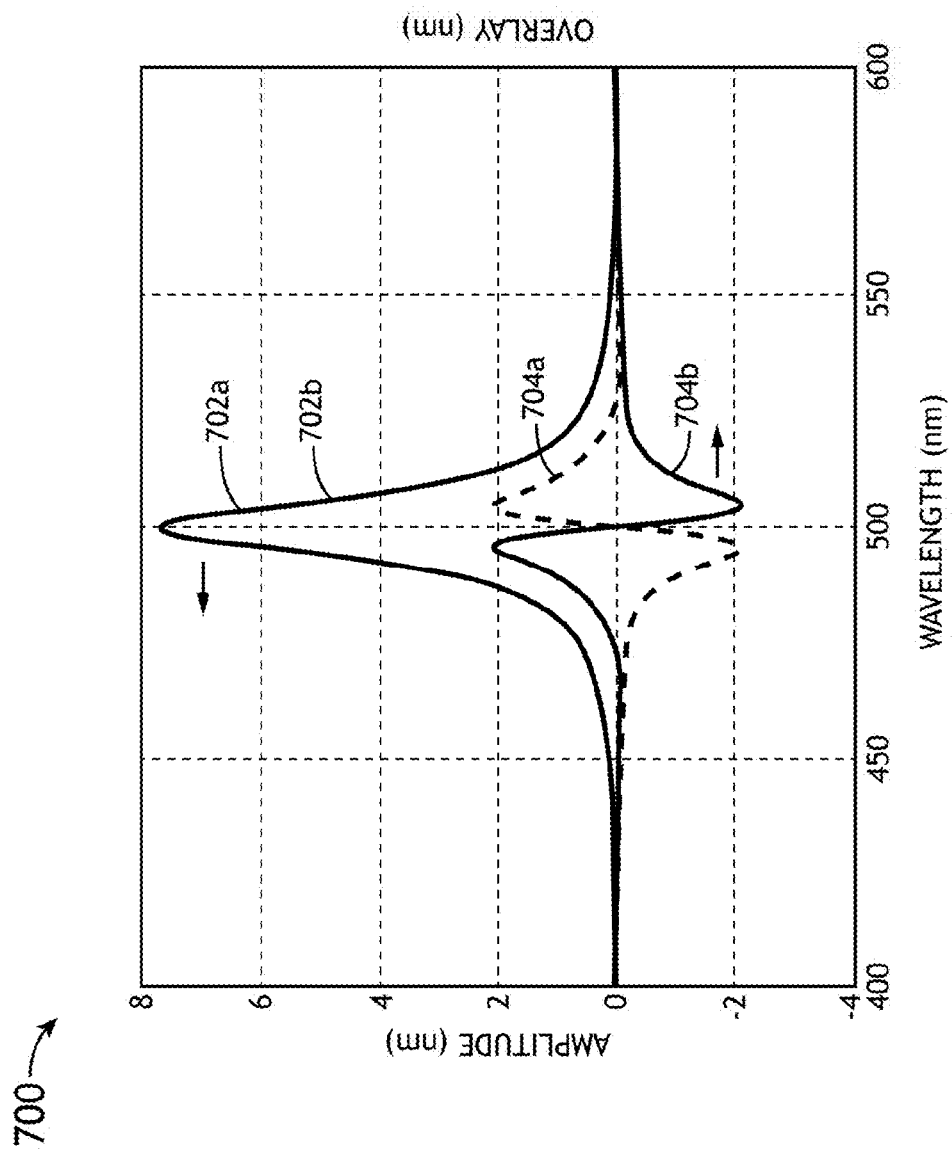
FIG. 7 includes metrology data of a scatterometry overlay metrology tool associated with two spatially separated metrology targets illustrating an asymmetric process variation with different directionalities between the two targets, in accordance with one or more embodiments of the present disclosure.

FIG. 7 includes metrology data 700 of a scatterometry overlay metrology tool associated with two spatially separated metrology targets illustrating an asymmetric process variation with different directionalities between the two targets, in accordance with one or more embodiments of the present disclosure. In one embodiment, metrology performance analysis module 206 may detect an asymmetric process variation with different directionalities (e.g. a variation between a right-leaning side-wall angle and a left-leaning side-wall angle, or the like) between spatially separated metrology targets by monitoring the sign of inaccuracy of the measured overlay associated with the grating-over-grating metrology target.

In another embodiment, resonance signals 702a, 702b illustrate a resonance associated with of the spatially separated first and second metrology targets, respectively. Further, error signals 704a, 704b illustrate corresponding inaccuracies of overlay measurements at the first and second metrology targets, respectively. For example, the sign of the inaccuracy (e.g. as characterized by a trend of overlay data as a function of location on the sample 106 or by comparison with a measurement using a robust recipe) may be different for asymmetric process variations of the same directionality. Further, as illustrated in FIG. 7, in one embodiment, an asymmetric process variation with different directionalities may not impact the resonance frequency in the pupil plane.

Figure 8:
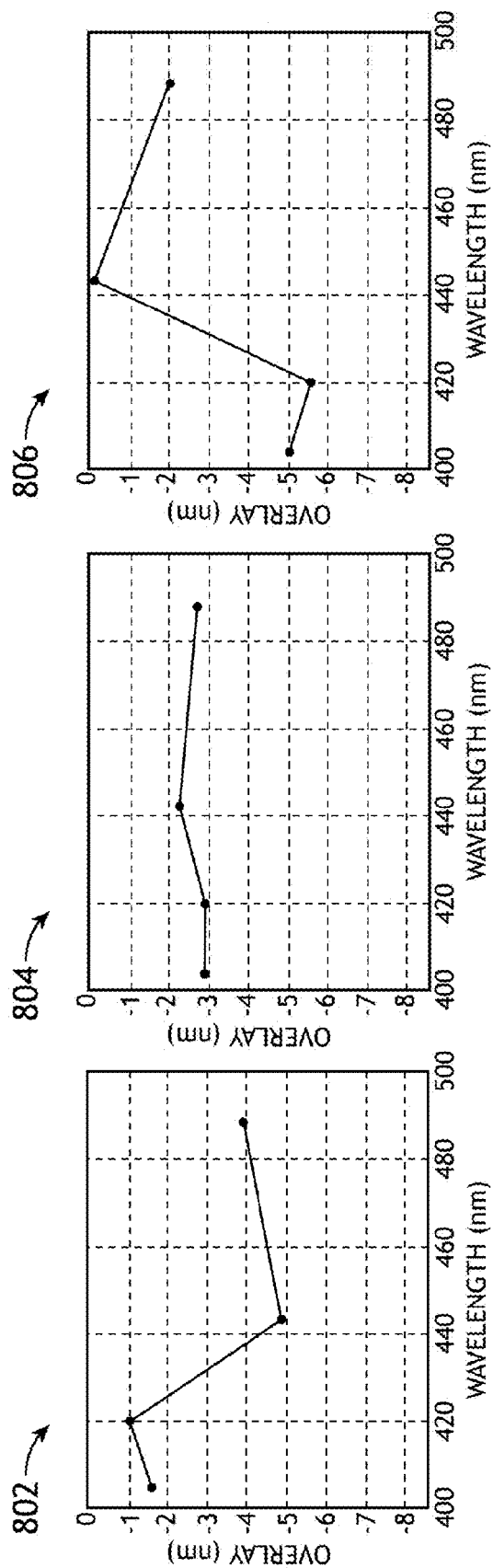
FIG. 8 includes overlay measurement signals associated with three spatially separated metrology targets on a sample including an asymmetric process variation, in accordance with one or more embodiments of the present disclosure.

FIG. 8 includes overlay measurement signals associated with three spatially separated metrology targets on a sample including an asymmetric process variation, in accordance with one or more embodiments of the present disclosure. In one embodiment, overlay measurements as a function of wavelength for a first, a second, and a third metrology target at spatially separated locations on the sample 106 are shown by overlay signals 802, 804, 806. For example, a metrology performance analysis module 206 may detect the direction of an asymmetric process variation (e.g. a side-wall angle variation that switches from left-leaning to right-leaning) by monitoring the trend of the overlay signals 802, 802, and 806 as a function of location on the sample 106. As shown in FIG. 8, in one embodiment, overlay signal 804 is approximately constant at around −3 nm of overlay error for all measured wavelengths (e.g. due to a weak or absent arc of discontinuity in the pupil plane). In another embodiment, overlay signal 802, associated with a different location on the sample 106, has a value of −1.8 nm at 405 nm, rising to −1 nm at 420 nm, falling to −4.9 at 445 nm, and rising to −4.1 at 490 nm. In another embodiment, a trend of overlay signal 806, associated with a third location on the sample 106, approximately mirrors the trend of overlay signal 802 around the overlay value of −3 nm. In this regard, the metrology performance analysis module 206 may identify a variation of the direction of an asymmetric process variation based on an analysis of the overlay signals 802, 804, 806 from the metrology tools 202. Further, the metrology performance analysis module 206 may determine that only a weak asymmetric process variation may be associated with the second metrology target (e.g. associated with overlay signal 804), whereas the asymmetric process variations associated with the first and third metrology targets (e.g. associated with overlay signals 802 and 806) have approximately the same strength, but opposite directionalities.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the disclosure is defined by the appended claims.

What is claimed:

1. A metrology performance analysis system, comprising:
   a metrology tool including one or more detectors; and
   a controller communicatively coupled to the one or more detectors, the controller including one or more processors configured to execute program instructions configured to cause the one or more processors to:
   receive one or more metrology data sets associated with a metrology target from the metrology tool, wherein the one or more metrology data sets include one or more measured metrology metrics, wherein the one or more measured metrology metrics indicate one or more deviations from one or more nominal values;
   simulate, via a perturbed geometric model, one or more variations of the one or more measured metrology metrics based on one or more selected semiconductor process variations;
   determine, based on the simulated one or more variations, one or more relationships between the one or more deviations from the one or more nominal values and the one or more selected semiconductor process variations; and
   determine one or more root causes of the one or more deviations from the one or more nominal values based on the one or more relationships between the one or more deviations from the one or more nominal values and the one or more selected semiconductor process variations.

2. The system of claim 1, wherein the one or more processors are further configured to execute program instructions configured to cause the one or more processors to:
   generate a geometric model of the metrology target;
   simulate one or more metrology metrics based on the geometric model of the metrology target; and
   generate the perturbed geometric model of the metrology target, wherein the perturbed geometric model includes one or more alterations of the metrology target caused by the one or more selected semiconductor process variations.

3. The system of claim 1, wherein the metrology target is an overlay target.

4. The system of claim 3, wherein the overlay target includes a grating-over-grating overlay target.

5. The system of claim 1, wherein the one or more metrology metrics include at least one of a pupil image metric, a precision metric, a tool-induced shift metric, a sensitivity metric, a diffraction efficiency metric, or a through-focus slope metric.

6. The system of claim 1, wherein the one or more metrology data sets include non-overlay data.

7. The system of claim 1, wherein the one or more selected semiconductor process variations include at least one of a film thickness variation, a real refractive index value associated with one or more wavelengths, an imaginary refractive index value associated with one or more wavelengths, a planarity variation, a stress variation, a strain variation, a critical dimension variation, a dishing variation, an erosion variation, or a side wall angle variation.

8. The system of claim 1, wherein the one or more processors are further configured to execute program instructions configured to cause the one or more processors to:
   modify a recipe of the one or more selected semiconductor processes based on the determined one or more root causes.

9. The system of claim 8, wherein the one or more processors are further configured to execute program instructions configured to cause the one or more processors to:
   modify the recipe of the one or more selected semiconductor processes by modifying at least one of a wavelength or a polarization of an illumination beam associated with the metrology tool.

10. The system of claim 1, wherein the one or more processors are further configured to execute program instructions configured to cause the one or more processors to:
    direct the metrology tool to replace the metrology target with an alternative metrology target, wherein the alternative metrology target is selected based on the determined one or more root causes.

11. The system of claim 10, wherein the one or more processors are further configured to execute program instructions configured to cause the one or more processors to:
    direct the metrology tool to replace the metrology target with the alternative metrology target to reduce the one or more deviations from the one or more nominal values.

12. The system of claim 1, wherein the metrology tool includes an ellipsometer.

13. The system of claim 12, wherein the ellipsometer includes at least one of a single-wavelength ellipsometer, a spectroscopic ellipsometer, or an angle-resolved ellipsometer.

14. The system of claim 13, wherein the ellipsometer includes a plurality of illumination beams directed to the metrology target at a plurality of angles of illumination.

15. The system of claim 13, wherein the spectroscopic ellipsometer measures Mueller matrix elements.

16. The system of claim 1, wherein the metrology tool includes a reflectometer.

17. The system of claim 16, wherein the reflectometer includes at least one of a single-wavelength reflectometer, a spectroscopic reflectometer, or an angle-resolved reflectometer.

18. The system of claim 1, wherein the metrology tool includes an imaging system.

19. The system of claim 18, wherein the imaging system includes at least one of a pupil imaging system or a spectral imaging system.

20. The system of claim 1, wherein the metrology tool includes an angle-resolved scatterometer with a pupil imaging system.

21. The system of claim 20, wherein the one or more measured metrology metrics are extracted from a pupil image, wherein the metrology target is a grating-over-grating structure.

22. The system of claim 21, wherein the one or more measured metrology metrics include a pupil feature in the pupil image.

23. The system of claim 22, wherein the one or more relationships between the one or more deviations from the one or more nominal values and the one or more selected semiconductor process variations include a variation of a location of the pupil feature in the pupil image associated with a symmetric selected semiconductor process variation.

24. The system of claim 22, wherein the one or more relationships between the one or more deviations from the one or more nominal values and the one or more selected semiconductor process variations include a variation of a strength of the pupil feature in the pupil image associated with an asymmetric selected semiconductor process variation.

25. The system of claim 22, wherein the one or more relationships between the one or more deviations from the one or more nominal values and the one or more selected semiconductor process variations include a variation of a sign of the pupil feature in the pupil image associated with a directionality of an asymmetric selected semiconductor process variation.

26. The system of claim 25, wherein the directionality of the asymmetric selected semiconductor process variation comprises:
   a directionality of a side wall angle asymmetry.

27. The system of claim 1, wherein the one or more processors are further configured to execute program instructions configured to cause the one or more processors to:
   generate a map of one or more values of the one or more measured metrology metrics at one or more locations on a wafer surface; and
   determine the one or more root causes based on the generated map.

28. The system of claim 1, wherein the metrology tool further comprises:
   an illumination source configured to generate an illumination beam;
   an imaging system configured to direct the illumination beam onto the metrology target; and
   one or more collection optics configured to capture at least a portion of the illumination beam incident on the metrology target to the one or more detectors to generate the one or more metrology data sets.

29. The system of claim 1, wherein the controller is integrated within the metrology tool.

30. A metrology performance analysis system, comprising:
   a metrology tool including one or more detectors; and
   a controller communicatively coupled to the one or more detectors, the controller including one or more processors configured to execute program instructions configured to cause the one or more processors to:
      receive one or more metrology data sets associated with a metrology target from the metrology tool, wherein the one or more metrology data sets include one or more measured metrology metrics, wherein the one or more measured metrology metrics indicate one or more deviations from one or more nominal values, wherein the one or more metrology data sets are generated using a first recipe;
      simulate, via a perturbed geometric model, one or more variations I of the one or more measured metrology metrics based on one or more selected semiconductor process variations;
      determine, based on the simulated one or more variations, one or more relationships between the one or more deviations from the one or more nominal values and the one or more selected semiconductor process variations;
      determine one or more root causes of the one or more deviations from the one or more nominal values based on the one or more relationships between the one or more deviations from the one or more nominal values and the one or more selected semiconductor process variations; and
      direct the metrology tool to generate one or more additional measured metrology metrics associated with at least one additional metrology target using a second recipe, wherein the second recipe reduces a sensitivity of the metrology tool to the one or more root causes.

31. The system of claim 30, wherein the one or more processors are further configured to execute program instructions configured to cause the one or more processors to:
   generate a geometric model of the metrology target;
   simulate one or more metrology metrics based on the geometric model of the metrology target; and
   a generate the perturbed geometric model of the metrology target, wherein the perturbed geometric model includes one or more alterations of the metrology target caused by the one or more selected semiconductor process variations.

32. A method for analyzing the performance of a metrology system, comprising:
   receiving one or more metrology data sets associated with a metrology target, wherein the one or more metrology data sets include one or more measured metrology metrics, wherein the one or more measured metrology metrics indicate deviations from one or more nominal values;
   simulating, via a perturbed geometric model, one or more variations of the one or more measured metrology metrics based on one or more selected semiconductor process variations;
   determining, based on the simulated one or more variations, one or more relationships between the one or more deviations from the one or more nominal values and the one or more selected semiconductor process variations; and
   determining one or more root causes of the one or more deviations from the one or more nominal values based on the one or more relationships between the one or more deviations from the one or more nominal values and the one or more selected semiconductor process variations.

33. The method of claim 32, further comprising:
   generating a geometric model of the metrology target;
   simulating one or more metrology metrics based on the geometric model of the metrology target; and
   generating the perturbed geometric model of the metrology target, wherein the perturbed geometric model includes one or more alterations of the metrology target caused by the one or more selected semiconductor process variations.

* * * * *